US008134028B2

(12) United States Patent
Osswald et al.

(10) Patent No.: US 8,134,028 B2
(45) Date of Patent: Mar. 13, 2012

(54) METHOD FOR PRODUCING 1,2-DIAMINO-3-METHYLCYCLOHEXANE AND/OR 1,2-DIAMINO-4-METHYLCYCLOHEXANE

(75) Inventors: Friederike Osswald, Mannheim (DE); Karl Heinz Brauch, Lampertheim (DE); Arnd Bottcher, Kuantan (MY); Jochem Henkelmann, Mannheim (DE); Frederik van Laar, Limburgerhof (DE); Till Gerlach, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 523 days.

(21) Appl. No.: 11/721,588

(22) PCT Filed: Dec. 14, 2005

(86) PCT No.: PCT/EP2005/013403
§ 371 (c)(1),
(2), (4) Date: Jun. 13, 2007

(87) PCT Pub. No.: WO2006/066762
PCT Pub. Date: Jun. 29, 2006

(65) Prior Publication Data
US 2009/0253938 A1      Oct. 8, 2009

(30) Foreign Application Priority Data

Dec. 17, 2004   (DE) .................. 10 2004 061 608

(51) Int. Cl.
   *C07C 211/00*      (2006.01)
(52) U.S. Cl. ...................................... 564/305
(58) Field of Classification Search .......... None
   See application file for complete search history.

(56) References Cited

U.S. PATENT DOCUMENTS

| 1,229,021 | A |   | 6/1917  | Blinck |
|-----------|---|---|---------|--------|
| 3,450,759 | A |   | 6/1969  | Cross et al. |
| 3,636,108 | A |   | 1/1972  | Brake |
| 4,049,584 | A | * | 9/1977  | Weissel .................. 502/313 |
| 4,321,354 | A |   | 3/1982  | Kluger et al. |
| 4,960,941 | A |   | 10/1990 | Vedage et al. |
| 5,026,914 | A |   | 6/1991  | Jenkins et al. |
| 5,214,212 | A |   | 5/1993  | Whitman |
| 5,874,622 | A | * | 2/1999  | Breitscheidel et al. ....... 564/450 |
| 5,973,207 | A |   | 10/1999 | Vedage |
| 5,981,801 | A |   | 11/1999 | Kim et al. |
| 6,043,395 | A |   | 3/2000  | Langer et al. |
| 6,075,167 | A |   | 6/2000  | Kim et al. |
| 6,429,338 | B1| * | 8/2002  | Burdeniuc et al. ............ 564/451 |

FOREIGN PATENT DOCUMENTS

| CA | 892636       | 2/1972  |
| DE | 2132547      | 1/1973  |
| EP | 0335272 A2   | 10/1989 |
| EP | 913388 A1    | 5/1999  |
| EP | 1329446 A2   | 7/2003  |
| JP | 59216852     | 12/1984 |

* cited by examiner

*Primary Examiner* — Daniel Sullivan
*Assistant Examiner* — Clinton Brooks
(74) *Attorney, Agent, or Firm* — Connolly Bove Lodge & Hutz LLP

(57) ABSTRACT

A process for preparing 1,2-diamino-3-methylcyclohexane and/or 1,2-diamino-4-methylcyclohexane by reacting 2,3- and/or 3,4-diaminotoluene with hydrogen at elevated pressure and elevated temperature in the presence of a heterogeneous rhodium catalyst, wherein a mixture comprising 2,3- and/or 3,4-diaminotoluene, a dialkyl ether and/or alicyclic ether as a solvent and ammonia is initially charged in an autoclave in the presence of the catalyst and subsequently hydrogenated while supplying hydrogen.

15 Claims, No Drawings

METHOD FOR PRODUCING 1,2-DIAMINO-3-METHYLCYCLOHEXANE AND/OR 1,2-DIAMINO-4-METHYLCYCLOHEXANE

RELATED APPLICATIONS

This application is a national stage application (under 35 U.S.C. §371) of PCT/EP2005/013403 filed Dec. 14, 2005, which claims benefit of German application 10 2004 061 608.6 filed Dec. 17, 2004.

The present invention relates to a process for preparing 1,2-diamino-3-methyl-cyclohexane and/or 1,2-diamino-4-methylcyclohexane by reacting 2,3- and/or 3,4-diaminotoluene with hydrogen at elevated pressure and elevated temperature in the presence of a heterogeneous rhodium catalyst.

1,2-Diaminomethylcyclohexanes, i.e. 1,2-diamino-3-methylcyclohexane and 1,2-diamino-4-methylcyclohexane, are important starting materials, especially for the production of hardeners (crosslinking agents) for epoxy resins. (Literature: for example U.S. Pat. No. 4,321,354 and J. W. Muskopf et al. "Epoxy Resins" in Ullmann's Encyclopedia of industrial Chemistry, 6th Edition, Vol. 12, pages 285-303).

The patent literature describes the ring hydrogenation of aromatic diamines comprehensively using the example of 4,4'-methylenedianiline (MDA) to 4,4'-methylenedicyclohexylamine (PACM). Toluenediamines and their hydrogenation are often also mentioned in general.

The following references are mentioned by way of example in this context:

U.S. Pat. No. 3,450,759, CA-B-892 636 (both Mobay Chem. Comp.), U.S. Pat. No. 3,636,108 (DuPont), DE-A-2 132 547 (BASF AG), JP-A-5 921 6852 (Nippon Kayaku), U.S. Pat. No. 4,960,941, U.S. Pat. No. 5,026,914 (both Air Products), U.S. Pat. No. 5,214,212 (Olin Corp.), U.S. Pat. No. 5,981,801 (Korea Institute of Technology), U.S. Pat. No. 5,973,207 (Air Products), U.S. Pat. No. 6,075,167 (Olin Corp.), U.S. Pat. No. 1,229,021 (Air Products).

The hydrogenation of the ortho-substituted toluenediamines (2,3- and 3,4-diamino-toluene) is not described explicitly in these patents.

The U.S. Pat. No. 3,450,759 teaches that the hydrogenation of the meta-toluene-diamines (2,4/2,6-toluenediamines) is possible only after preceding removal of the ortho-toluenediamines, since these act as a catalyst poison. It is assumed that these compounds with their adjacent amino functions form chelate complexes with the active metal and thus irreversibly cover the surface of the catalyst.

In the U.S. Pat. No. 5,973,207, Air Products described an improved hydrogenation process of the meta-toluenediamines without preceding removal of the small amounts of ortho-toluenediamines.

A first explicit description of the hydrogenation of vicinal toluenediamines was published by Air Products 2002 in the U.S. Pat. No. 6,429,338 (equivalent: EP-A-1 329 446). According to this, the hydrogenation of the diamines is achieved by combining three essential features: use
a) of an Rh catalyst,
b) of a $C_{4-12}$-dialkyl ether as a solvent and
c) a semibatchwise method in which the toluenediamine is fed slowly into the autoclave during the hydrogenation.

A disadvantage can be the feeding of the substance to be hydrogenated, i.e. this semibatchwise method. An increased level of apparatus and/or measurement and control complexity can be associated with a semibatchwise method compared to a batchwise method, for example a heated receiver or a heated metering line for the toluenediamine.

It is an object of the present invention to find an improved economically viable process for preparing 1,2-diaminomethylcyclohexanes. The diamines, 1,2-diamino-3-methyl-cyclohexane and/or 1,2-diamino-4-methylcyclohexane, should be obtained in a high yield, in particular space-time yield, selectivity, purity and/or color quality.

[Space-time yields are reported in "amount of product/(volume of catalyst•time)" $(kg/(l_{cat.} \cdot h))$ and/or "amount of product/(reactor volume•time)" $(kg/(l_{reactor} \cdot h))$].

Accordingly, a process has been found for preparing 1,2-diamino-3-methylcyclohexane and/or 1,2-diamino-4-methylcyclohexane by reacting 2,3- and/or 3,4-diaminotoluene with hydrogen at elevated pressure and elevated temperature in the presence of a heterogeneous rhodium catalyst, which comprises initially charging a mixture comprising 2,3- and/or 3,4-diaminotoluene, a dialkyl ether and/or alicyclic ether as a solvent and ammonia in an autoclave in the presence of the catalyst and subsequently hydrogenating while supplying hydrogen.

The process according to the invention is preferably a batchwise method and not a semibatchwise method (semicontinuous method). In other words, the 2,3- and/or 3,4-diaminotoluene to be hydrogenated is initially charged completely in the autoclave and preferably no 2,3- and/or 3,4-diaminotoluene is fed to the autoclave during the hydrogenation.

The invention has recognized the advantageous procedure in the presence of ammonia The use of $NH_3$ as an additive makes it possible to carry out the hydrogenation batchwise (batchwise mode) in an advantageous manner. The catalyst remains active and stable even at relatively high toluenediamine concentrations in the reaction medium.

The process according to the invention can be performed as follows:

The 2,3- and/or 3,4-diaminotoluene feedstock is used preferably in a purity of ≧90% by weight, in particular ≧98% by weight, for example from 98.2 to 99.9% by weight. Such purities can be achieved, for example, by distillation or rectification of commercially available material.

The solvent used is preferably a $C_{4-12}$-dialkyl ether and/or $C_{3-12}$-alicyclic ether, in particular a $C_{4-6}$-dialkyl ether and/or $C_{4-6}$-alicyclic ether. Examples of these are methyl tert-butyl ether (MTBE), diethyl ether (DEE), di-n-propyl ether, di-n-butyl ether, 1,2-dimethoxyethane, 1,2-diethoxyethane tetrahydrofuran (THF), 2-methyl-THF, tetrahydropyran, 1,3-dioxepane, 1,4-dioxane, 1,3-dioxane and 1,3-dioxolane. Particular preference is given to THF.

Preference is given to using a from 5 to 50% by weight, particularly from 10 to 40% by weight, especially from 20 to 25% by weight, solution of the diaminotoluene or of the two diaminotoluenes (in total) in the solvent.

The solvent used may also be a mixture of two or more of the dialkyl ethers and/or alicyclic ethers mentioned.

Optionally, further inert solvents such as aliphatic or cycloaliphatic solvents may be present in the inventive hydrogenation process Examples of these are $C_{5-8}$ hydrocarbons such as n-pentane, n-hexane and cyclohexane.

Preference is given to using, together with the diaminotoluene(s), lithium hydroxide (LiOH), in particular from 0.1 to 5 mol % of LiOH, very particularly from 0.5 to 1.5 mol % of LiOH, more preferably from 0.8 to 1.2 mol %, for example 1 mol %, of LiOH, based in each case on the diaminotoluene or the two diaminotoluenes (in total).

In a preferred embodiment, the appropriate amount of LiOH is used in the form of an aqueous solution, for example in the form of a from 5 to 20% by weight aqueous solution.

The hydrogenation is carried out in the presence of ammonia. Preference is given to using from 5 to 500 mol %, in particular from 250 to 350 mol %, very particularly from 280 to 320 mol %, for example 300 mol %, of ammonia, based in each case on the diaminotoluene or the two diaminotoluenes (in total).

The hydrogenation is effected in particular at temperatures in the range from 130 to 220° C., very particularly from 140 to 195° C.

The absolute pressure employed in the hydrogenation is in particular in the range from 100 to 300 bar, very particularly from 200 to 280 bar.

The heterogeneous rhodium catalysts used may be Rh catalysts which are customary on the market. The catalyst may also be prepared by processes known to those skilled in the art.

An example of a suitable commercially available catalyst is:

5% Ru/$Al_2O_3$ (Aldrich product numbers: 21,285-7; 37,971-9).

Preferred catalysts comprise in the range from 1 to 25% by weight, in particular in the range from 2 to 5% by weight, of rhodium based on the support material.

In addition, the catalyst can comprise further metals such as Ru, Pd, Ni, Fe, Ir and/or Co, for example in amounts in the range from 0.01 to 5% by weight (in total), in particular in the range from 0.1 to 2.5% by weight, based on the support material.

Preferred catalysts comprise kappa-, delta- and/or gamma-alumina as the support material.

In a particular embodiment, the support material consists of kappa-, delta- and/or gamma-alumina.

A particularly preferred support material is gamma-alumina. This is obtainable, for example, from BASF AG (D10-10).

A very particularly preferred catalyst consists of gamma-alumina as the support material and rhodium.

In a particular embodiment, the rhodium catalyst used is treated beforehand with lithium hydroxide. This treatment is particularly advantageous when the hydrogenation is carried out in the presence of LiOH in the initially charged reaction mixture.

This treatment of the catalyst with LiOH can be effected by processes known to those skilled in the art, for example by saturating the catalyst with LiOH, for example from 0.01 to 5.0% by weight of LiOH (based on the support material), in the presence of a suitable solvent, for example water (EP-A1-913 388, U.S. Pat. No. 6,429,338, U.S. Pat. No. 3,636,108).

The reactors used for the process according to the invention may, for example, be customary high-pressure autoclaves.

After the process according to the invention has been carried out, the product or the products can be isolated, for example, by distillation.

In one embodiment, the process product which is obtained may advantageously be used without further workup as a crosslinking agent or component in a crosslinking agent for epoxy resins.

The conversions of diaminotoluene achievable by the process according to the invention are in the region of ≧95%, in particular ≧99%, for example from ≧96 to 99.9% or from 99.5 to 100%, at selectivities (for the formation of 1,2-diamino-3-methyl-cyclohexane and/or 1,2-diamino-4-methyl-cyclohexane) in the region of ≧80%, in particular ≧85%, for example from 86 to 99.5% or from 90 to 99%.

EXAMPLES

Preparation of an Rh/gamma-$Al_2O_3$ Catalyst
(Catalyst A)

A spray-impregnation solution was prepared by dissolving rhodium trichloride (Degussa; batch No. 26661, comprising 37.9% Rh) in water until a volume was obtained which was 30% of the water absorption capacity. This solution was sprayed onto gamma-$Al_2O_3$ from BASF AG (D10-10; water absorption capacity: 5.8 ml of water per 10 g of D10-10) as a support and subsequently dried under motion at 120° C. for 12 h.

The dried catalyst precursor was reduced in a hydrogen stream at 300° C. for 4 h. After cooling to room temperature, the reduced catalyst was passivated (air in $N_2$). It was ensured that the temperature remained below 40° C. The thus prepared catalyst comprised 3% by weight of Rh.

Hydrogenation a) General Experimental Procedure

The feedstock, vicinal toluenediamine, was obtained from BASF Schwarzheide GmbH and had been removed in a distillation overhead from the high-boiling 2,4/2,6-toluenediamine isomer mixture. Air contact during the transfer operation resulted in a dark brown color of the solid. The purity was 99.3% (CC area percent).

The weighed-out amount of the vicinal toluenediamine was dissolved in THF and introduced together with a certain amount of catalyst (in powder form) into a 0.3-liter (or 1.2-liter) autoclave. The autoclave was sealed and a pressure test up to 250 bar with nitrogen was done. After the autoclave had been decompressed, a pressure of 50 bar of hydrogen was established and it was heated to reaction temperature. After the temperature had been obtained, hydrogen was injected to 250 bar. The hydrogenation time began. During the reaction, falling pressure was balanced by injecting further hydrogen. After the hydrogenation time had ended, the autoclave was decompressed and the reaction mixture was discharged under nitrogen. A sample was taken, the catalyst was removed by means of filtration and the filtrate was analyzed by gas chromatography. By-products which are formed are denoted as
a) monomer=methylcyclohexylamine, formed by ammonia elimination of the product and
b) dimer=N,N-bis(aminomethylcyclohexyl)amine and/or N,N-bis(aminomethylphenyl)amine, formed by condensation of two product or reactant molecules.
b) Addition of Various Additives
Experiment A: No additives
Experiment B: Addition of lithium hydroxide
Experiment C: Addition of ammonia
Experiment D: Addition of lithium hydroxide and ammonia 150 ml of a 20% by weight solution of the vicinal toluenediamine in THF, 1.5 g of catalyst A (3% by weight of Rh/$Al_2O_3$) and 0.6 g of 10% by weight aqueous lithium hydroxide solution (Experiments B and D) or 20 ml of ammonia (Experiments C and D) were initially charged in a 0.3-liter autoclave. At 180° C. and 250 bar, hydrogenation was effected for 5 hours (experiments B and D) or for 4 hours (experiment A) or for 11 hours (experiment C).

Results

| Experiment | Reactant [%] | Product [%] | Diamine [%] | Monoamine [%] |
|---|---|---|---|---|
| A | 1 | 54 | 38 | 7 |
| B | <0.1 | 81 | 11 | 8 |

-continued

| Experiment | Reactant [%] | Product [%] | Diamine [%] | Monoamine [%] |
|---|---|---|---|---|
| C | 5 | 65 | 19 | 11 |
| D | 0.2 | 89 | 4 | 7 |

Product = 3-methylcyclohexane-1,2-diamine or 4-methylcyclohexane-1,2-diamine
Diamine = N,N-bis(aminomethylcyclohexyl)amine and/or N,N-bis(aminomethylphenyl)amine,
Monoamine = methylcyclohexylamine The hydrogenation proceeded unselectively without addition of additives, since condensation products were formed to a relatively large degree. In the presence of ammonia, the reaction proceeded slowly and more selectively. Lithium hydroxide increased the activity and the selectivity of the catalyst. The best results with regard to a full and selective reaction were achieved by the combination of the ammonia and lithium hydroxide additives.

What is claimed is:

1. A process for preparing 1,2-diamino-3-methylcyclohexane and/or 1,2-diamino-4-methylcyclohexane, comprising the steps of
    (a) charging an autoclave with a mixture comprising 2,3- and/or 3,4-diaminotoluene, a dialkyl ether and/or alicyclic ether as a solvent, ammonia, and a heterogeneous rhodium catalyst; and
    (b) hydrogenating said 2,3- and/or 3,4-diaminotoluene by supplying hydrogen to said autoclave at elevated pressure and elevated temperature to form 1,2-diamino-3-methylcyclohexane and/or 1,2-diamino-4-methylcyclohexane;
wherein said process is performed batchwise.

2. The process according to claim 1, wherein said mixture additionally comprises lithium hydroxide.

3. The process according to claim 2, wherein said lithium hydroxide is used in the form of an aqueous solution.

4. The process according to claim 1, wherein a $C_4$ to $C_{12}$ dialkyl ether and/or a $C_3$ to $C_{12}$ alicyclic ether is used as the solvent.

5. The process according to claim 4, wherein tetrahydrofuran is used as the solvent.

6. The process according to claim 1, wherein step (b) is carried out at an absolute pressure in the range of from 100 to 300 bar.

7. The process according to claim 1, wherein step (b) is carried out at a temperature in the range of from 130 to 220° C.

8. The process according to claim 1, wherein said 2,3- and/or 3,4-diaminotoluene is used as a 5 to 50% by weight solution in said solvent.

9. The process according to claim 1, wherein said ammonia is used in an amount of from 5 to 500 mol % based on the amount of 2,3- and/or 3,4-diaminotoluene.

10. The process according to claim 2, wherein said lithium hydroxide is used in an amount of from 0.1 to 5 mol % based on the amount of 2,3- and/or 3,4-diaminotoluene.

11. The process according to claim 1, wherein said heterogeneous rhodium catalyst comprises rhodium and a support material and wherein said rhodium is used in an amount of from 1 to 25% based on the amount of said support material.

12. The process according to claim 1, wherein said heterogeneous rhodium catalyst comprises a kappa-, delta-, and/or gamma-alumina support material.

13. The process according to claim 1, wherein said heterogeneous rhodium catalyst consists of rhodium and gamma-alumina.

14. The process according to claim 1, wherein said heterogeneous rhodium catalyst is pretreated with lithium hydroxide.

15. The process according to claim 1, wherein said 2,3- and/or 3,4-diaminotoluene has a purity of greater than or equal to 90% by weight.

* * * * *